(12) United States Patent
Aho et al.

(10) Patent No.: US 7,717,661 B1
(45) Date of Patent: May 18, 2010

(54) COMPACT MULTIPLE DIAMETERS WAFER HANDLING SYSTEM WITH ON-CHUCK WAFER CALIBRATION AND INTEGRATED CASSETTE-CHUCK TRANSFER

(75) Inventors: Marc T. Aho, Mountain View, CA (US); Thaddeus J. Wilson, Sunnyvale, CA (US)

(73) Assignee: n&k Technology, Inc., San Jose, CA (US)

( * ) Notice: Subject to any disclaimer, the term of this patent is extended or adjusted under 35 U.S.C. 154(b) by 532 days.

(21) Appl. No.: 11/420,470

(22) Filed: May 25, 2006

(51) Int. Cl.
*B65B 21/02* (2006.01)
*B65G 65/04* (2006.01)
*G01B 11/00* (2006.01)
*G01N 21/86* (2006.01)

(52) U.S. Cl. .............. 414/416.03; 414/226.05; 414/936; 414/937; 414/779; 356/400; 356/614; 257/E21.525; 250/559.3

(58) Field of Classification Search .............. 135/568.2, 135/568.21; 414/416.01, 416.03, 416.05, 414/416.06, 416.08, 416.12, 808, 810, 811, 414/936, 940, 941; 700/218; 901/16, 20, 901/24; 356/614
See application file for complete search history.

(56) References Cited

U.S. PATENT DOCUMENTS

| | | | | |
|---|---|---|---|---|
| 4,425,075 A * | 1/1984 | Quinn | ................. | 414/755 |
| 4,539,695 A * | 9/1985 | La Fiandra | ................. | 378/34 |
| 4,770,590 A | 9/1988 | Hugues et al. | | |
| 5,194,743 A * | 3/1993 | Aoyama et al. | ............. | 250/548 |
| 5,238,354 A * | 8/1993 | Volovich | ............. | 414/779 |
| 5,365,672 A * | 11/1994 | Kato | ............. | 33/520 |
| 5,456,561 A | 10/1995 | Poduje et al. | | |
| 5,513,948 A * | 5/1996 | Bacchi et al. | ............. | 414/783 |
| 5,851,102 A | 12/1998 | Okawa et al. | | |
| 5,870,488 A | 2/1999 | Rush et al. | | |
| 5,944,476 A | 8/1999 | Bacchi et al. | | |
| 6,340,281 B1 * | 1/2002 | Haraguchi et al. | ............. | 414/783 |
| 6,400,445 B2 * | 6/2002 | Nishi et al. | ............. | 355/72 |
| 6,532,975 B1 | 3/2003 | Kamikawa et al. | | |
| 6,533,521 B1 | 3/2003 | Todorov et al. | | |
| 6,624,393 B2 | 9/2003 | Howell et al. | | |
| 6,722,840 B2 | 4/2004 | Fujisawa et al. | | |
| 6,747,746 B2 | 6/2004 | Chizhov et al. | | |
| 6,811,370 B2 * | 11/2004 | Buermann | ............. | 414/416.03 |
| 2005/0111944 A1 * | 5/2005 | Aho et al. | ............. | 414/416.01 |

\* cited by examiner

*Primary Examiner*—Gregory W Adams
(74) *Attorney, Agent, or Firm*—Lumen Patent Firm (57) ABSTRACT

A compact multiple diameter wafer testing device with a footprint of about 33 by 34 inches features on-chuck wafer calibration and integrated cassette-chuck transfer. It includes a five axes wafer handling system, a quick exchange chuck and a fixed through beam sensor fixed. Two of the five axes are provided by an X-Y stage, a third axis is provided by a rotary stage on top of the X-Y stage, a fourth axis belongs to a rotating effector and a fifth axis is provided by motion controlled pin lifters all combined with the X-Y stage. The quick exchange chuck may be easily changed for different wafer diameters and also calibrated by the through beam sensor. The through beam sensor provides on-chuck position calibration of the chucked wafers in conjunction with the X-Y stage and rotary stage. The compact wafer testing device handles wafers between six and twelve inches diameter.

12 Claims, 7 Drawing Sheets

COMPACT MULTIPLE DIAMETERS WAFER HANDLING SYSTEM WITH ON-CHUCK WAFER CALIBRATION AND INTEGRATED CASSETTE-CHUCK TRANSFER

FIELD OF INVENTION

The present invention relates to compact surface testing devices for wafers of multiple diameters with on-chuck wafer calibration and integrated cassette-chuck transfer.

BACKGROUND OF INVENTION

Ever increasing competition in cost effective semiconductor fabrication results in a continuous demand for more compact and versatile fabrication devices. A significant step during semiconductor fabrication is the repeated inspection of the wafer surfaces during intermediate fabrication of semiconductor features as are well known in the art. For that purpose, wafers need to be inspected with high throughput rates. In the prior art, a number of wafer testing devices are provided with differing complexity and space consumption to provide more or less automated wafer inspection. Wafer testing devices need to operate within expensive laboratory space. One aspect of cost efficient wafer testing is the minimum required footprint of a wafer testing device. As result, compact wafer testing devices with a footprint of less than 3 by 3 feet have been introduced in the prior art. The downside of compact wafer testing devices may be reduced through put due to separate well known wafer pre alignment and/or eventual additional need for external robotic devices for wafer transfer between a chuck at which the wafer is fixed for inspection and a cassette where a number of wafers are stacked for transport between fabrication stages. Therefore, there exists a need for a compact wafer testing device without need for pre alignment outside the device's main footprint and integrated cassette-chuck transfer. The present invention addresses this need.

At the time of this invention, wafers for semiconductor fabrication are utilized in 150 mm, 200 mm and 300 mm diameters. Therefore and to maximize the functionality of a compact wafer testing device, there exists a need for a compact wafer testing device capable of testing wafers of multiple diameters with minimum modifications. The present invention addresses this need.

There are a number of wafer cassette systems including cassette elevators commercially available that are optimized for different size wafers and other fabrication particularities as are well known to anyone skilled in the art. Therefore, there exists a need for of compact wafer testing device that provides an interface for integrating one or more freely selectable commercial cassette elevators and respective cassette systems. The present invention addresses also this need.

SUMMARY

A compact testing device with a footprint of about 33 by 34 inches is configured for testing multiple contours flat objects in the preferred configuration of wafers having between three and six inches minimum and maximum contour-center distances. The testing device includes a five axes computer numeric controlled wafer handling system, a quick exchange chuck and a through beam edge detector. The five axes are first and second linear chuck position axes provided by an X-Y stage, a third rotational chuck positioning axis provided by a rotary stage on top of the X-Y stage, a fourth vertical effector rotation axis of a motion controlled effector rotation device also combined with the X-Y stage, and a fifth vertical chuck-effector transfer axis provided by at least three motion controlled pin lifters combined with the X-Y stage. Also part of the wafer handling system are a cassette elevator controller and one or more cassette elevator docketing interface(s) for docketing preferably commercially available cassette elevator(s) to the testing device.

The fourth axis is positioned with respect to the third axis and the effector is of a length such that the effector may reach through the docketing interface and may access an up to a 300 mm diameter wafer from a cassette vertically moved in a cassette elevator peripherally attached to the docking interface and such that the effector may rotationally position a wafer with respect to the X-stage into substantial concentric alignment with the third axis.

On-chuck calibration of the wafer fixed on a chucking face of the chuck is provided by a through beam edge detector sensor combined with the testing device. The through beam sensor is horizontally positioned in conjunction with the maximum and minimum contour-center distances of the chucked wafer. Position calibration of the wafer is accomplished in conjunction with a combined movement of the fixed wafer via the X-Y stages along first and second axes and via the rotary stage around the third axis. The on-chuck wafer position calibration eliminates the need for a separate prealigner placed within or outside the overall footprint of the testing device. Changing of tested wafer diameter is made possible without need for adjusting or modifying the prealigner.

DETAILED DESCRIPTION

Figure 1:
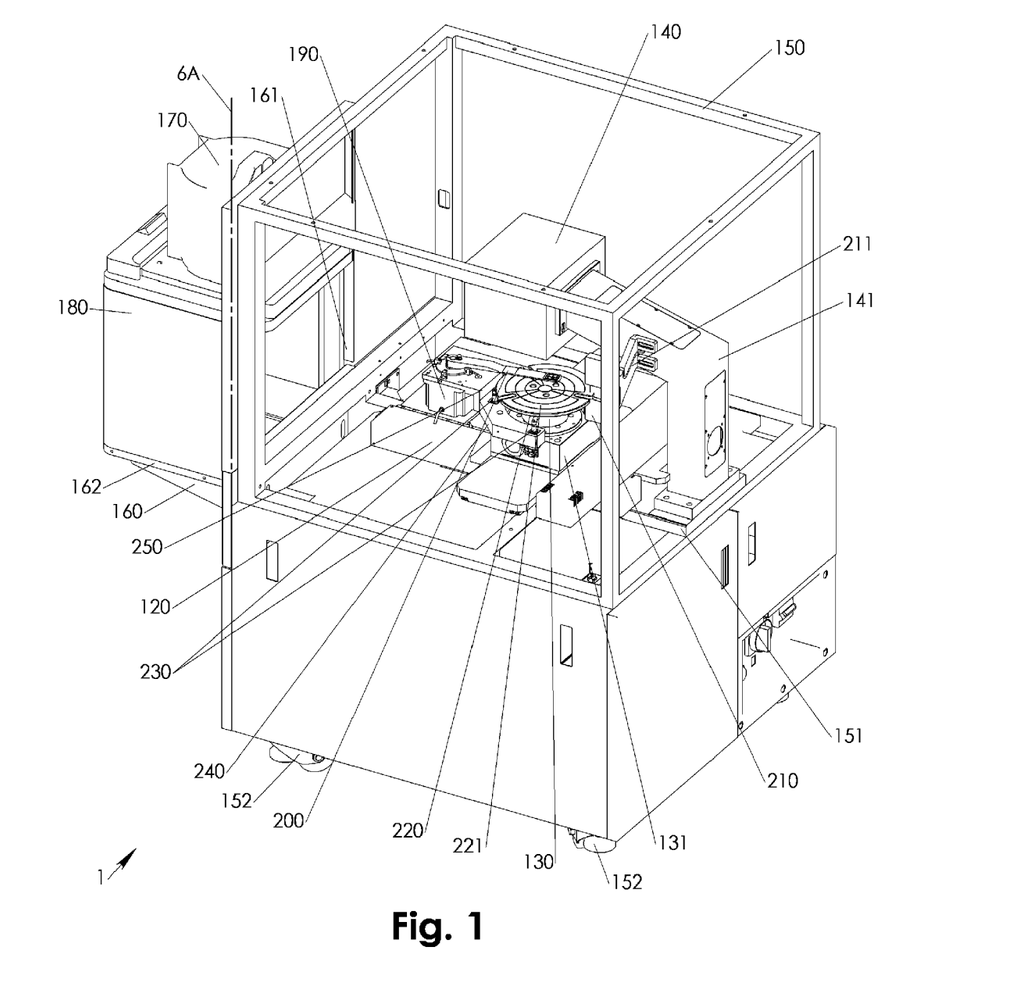
FIG. 1 is a first perspective view of a preferred embodiment of the invention.
Figure 2:
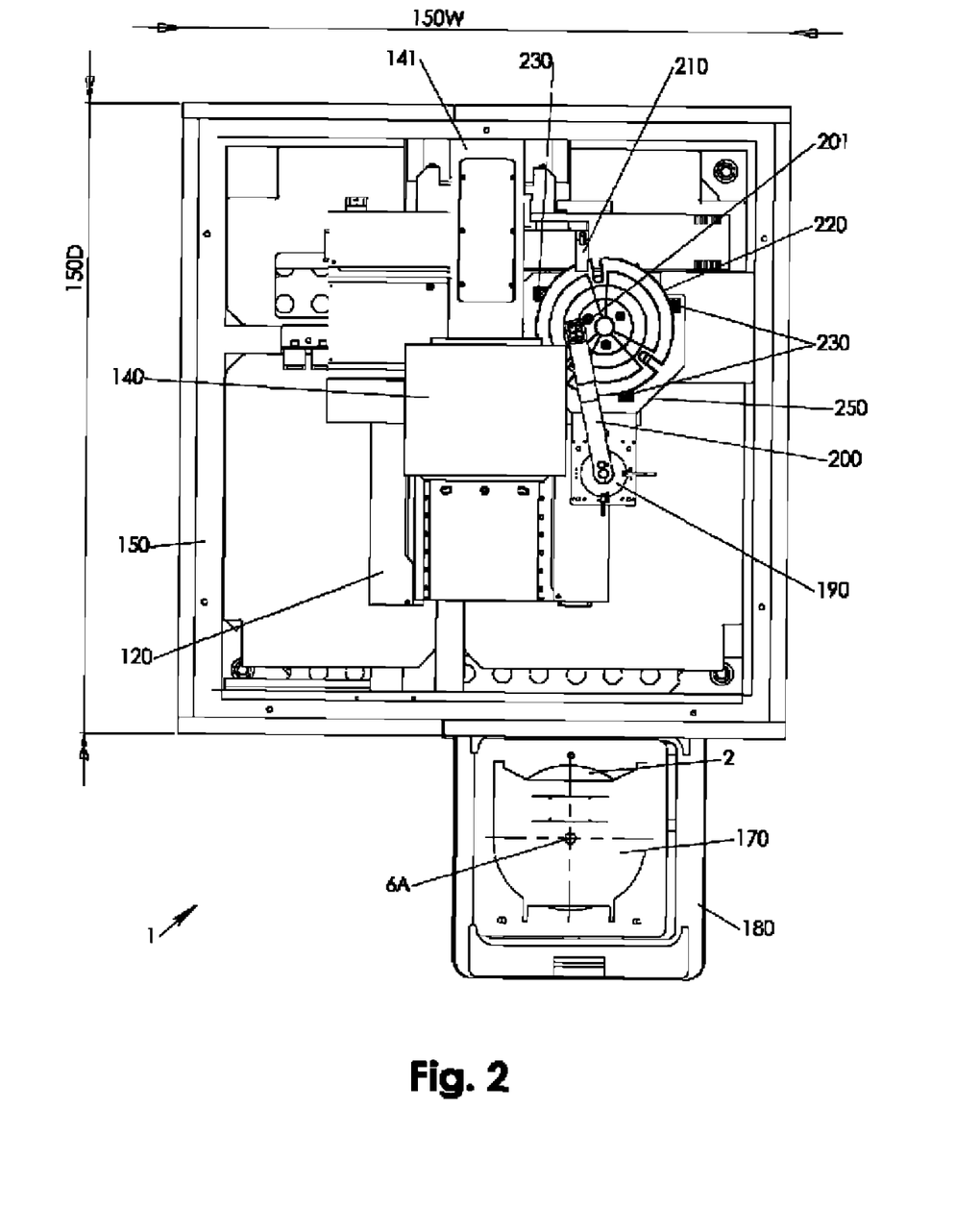
FIG. 2 is a top view of the device of FIG. 1.
Figure 3:
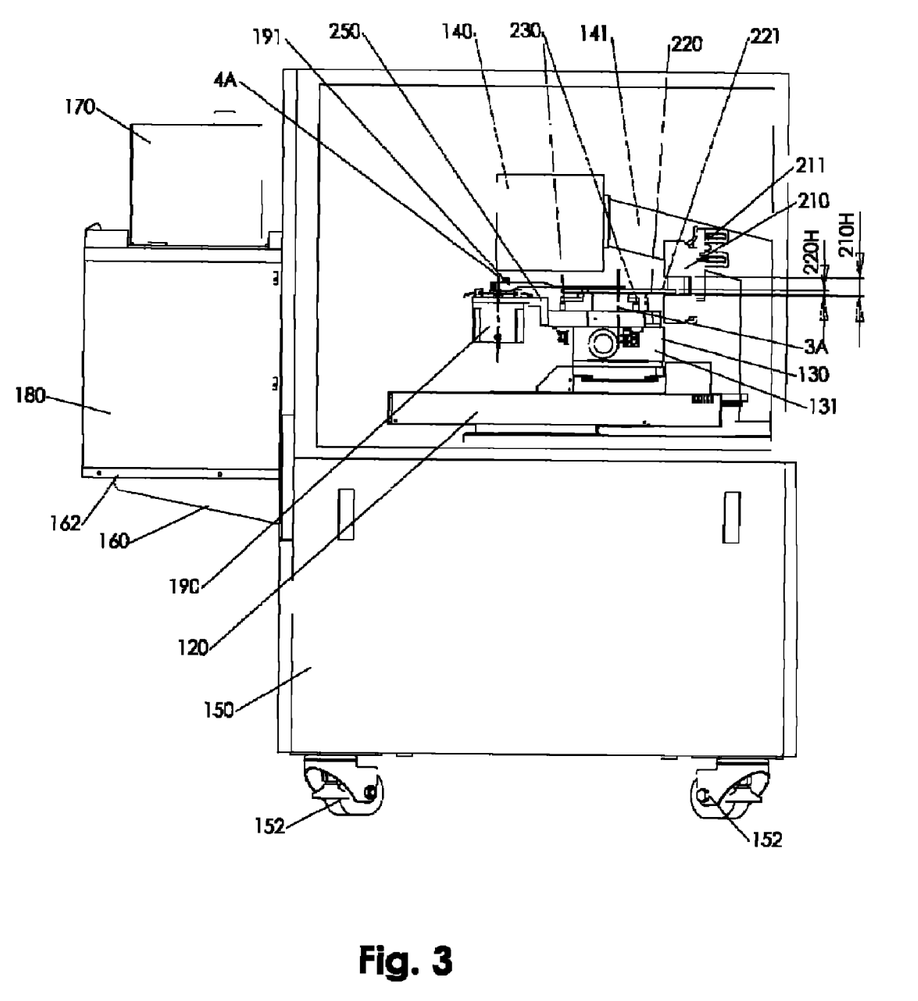
FIG. 3 is a side view of the device of FIG. 1.
Figure 7:
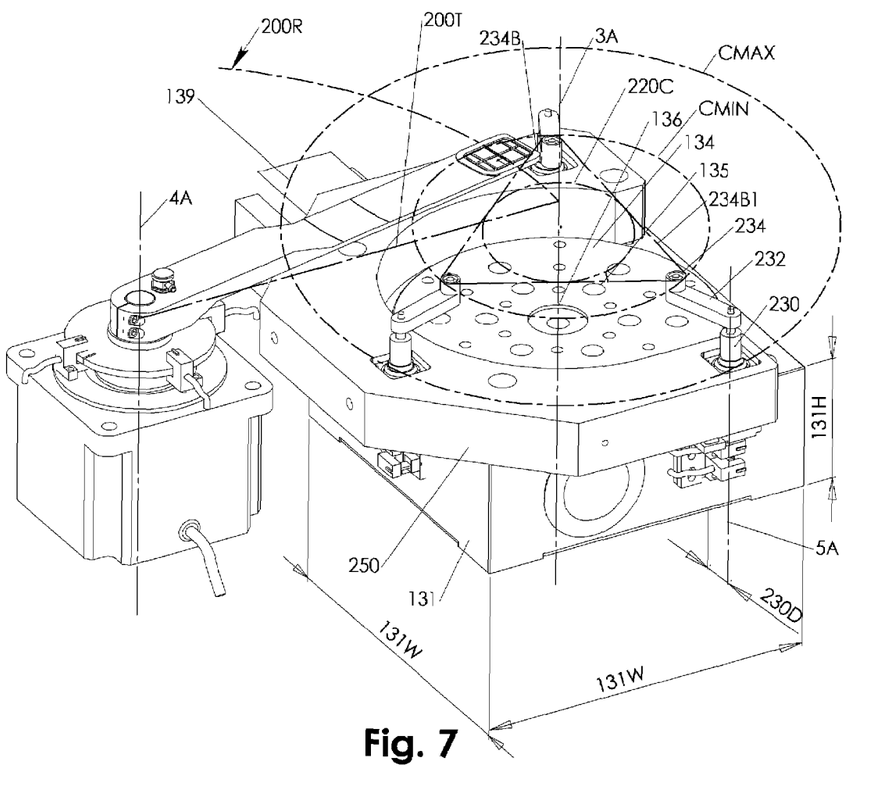
FIG. 7 is the second perspective view of the subassembly of FIG. 6 without chuck and flange angle.

Referring to FIGS. 1-3, a compact flat object 2 testing device 1 may be a well known reflectance optical surface testing device in which flat objects 2 of multiple contours may be tested. Multiple contours flat objects 2 in context with the present invention are intermediate semiconductor fabrication structures such as preferably well known wafers but may also include well known photomasks for fabricating features on wafers as is well known in the art. As shown in FIG. 7, the flat objects 2 may have a maximum contour-center distance CMAX of preferably six inches and a minimum contour-center distance CMIN of preferably three inches. In case of wafers, the minimum contour-center distance CMIN is half of the wafers diameter such as 150 mm, 200 mm, 300 mm diameter standards with which wafers are used in the industry at the time this invention was made. The compact multiple contours flat objects 2 surface testing device 1 features preferably within an overall footprint 150W by 150D of about 33 by 34 inches on-chuck object calibration and integrated cassette-chuck transfer as will be described in more detail below. Cover panels and other well known portions of the compact testing device 1 such as attachment features are hidden for the purpose of clarity and for visualizing central operational parts. Other well known elements such as a vacuum system, cover plates, window flanges, handles, ventilation openings, and the like are also depicted in the FIGS. 1-5.

The compact testing device 1 includes a frame 150 with which a base plate 151 is combined. Wheels 152 may provide for easy positioning of the compact testing device 1. Attached to and/or part of the frame 150 is a cassette elevator docking interface 160 for peripherally attaching preferably a commercially available cassette elevator 180 to the compact testing device 1 at an interface flange 161 through which an effector 200 may transfer a flat object 2 from/to a cassette 170 lowered into access position. In the FIGS. 1-3, the cassette 170 is depicted in exchange position on top of cassette elevator 180. In order for the effector 200 to transfer a flat object 2 from/to a predetermined storage compartment of the cassette 170, the cassette 170 may be vertically moved by the cassette elevator 180, which is controlled by a well known computer control of the testing device 1.

The cassette elevator 180 may preferably be a commercially available product such as a well known SMIF loadport made by companies such as Asyst™ or Brooks Automation™. SMIF cassette elevators 180 may handle 150 mm and 200 mm wafers as well as 6"×6" photomasks. Other companies make these type cassette elevators 180 that are used to open well known SEMI standard SMIF PODS. SMIF PODS are plastic containers that hold multiple wafers cassettes 170 in sealed environment. When they are loaded onto the SMIF loadport, a bottom door is opened and the cassette 170 full of wafers is vertically translated down. The Asyst™ loadport for example checks for protruding wafers, scans the cassette 170 to see, which slots have wafers, and provides for vertical adjustment of the cassette 170. The depicted cassette 170 and cassette elevator 180 handle 200 mm diameter wafers. To handle 300 mm wafers for which to the inventors knowledge no cassette elevators are commercially available at the time this invention was made, a custom cassette elevator may be integrated in and combined with the testing device 1 instead of the cassette elevator docking interface 160.

Attachment standards of cassette elevators 180 may vary with brand and size of handled wafers. In case of photomasks, different cassettes 170 and cassette elevators 180 may be used as is well known in the art. The docking interface 160 features an interface base 162 mainly for weight support and vertical positioning of the cassette elevator 180. The interface flange 161 holds the cassette elevator 180 in horizontal position and substantially seals the interior of the testing device 1 with the cassette elevator 180.

Figure 4:
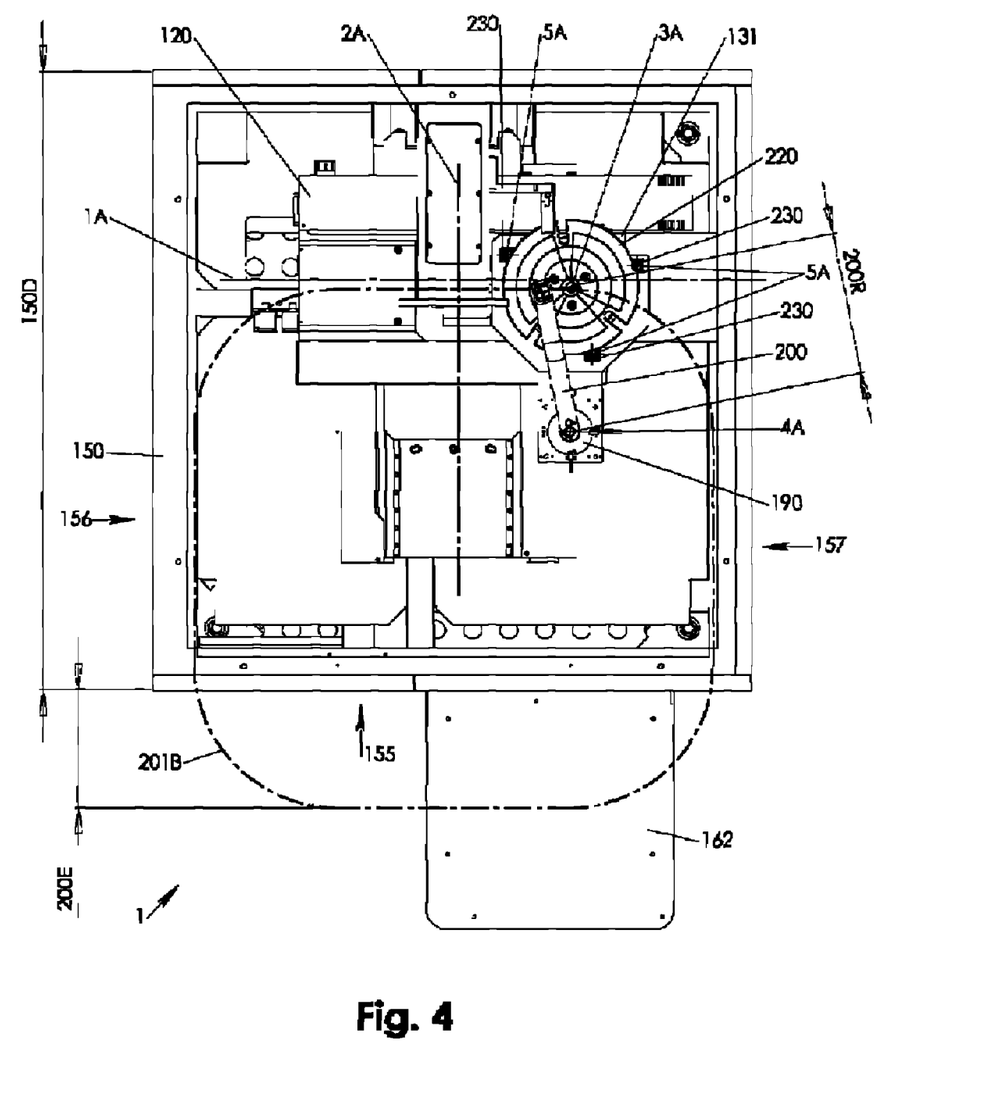
FIG. 4 is a top view of the device of FIG. 1 without cassette, cassette elevator and without optical testing head.
Figure 5:
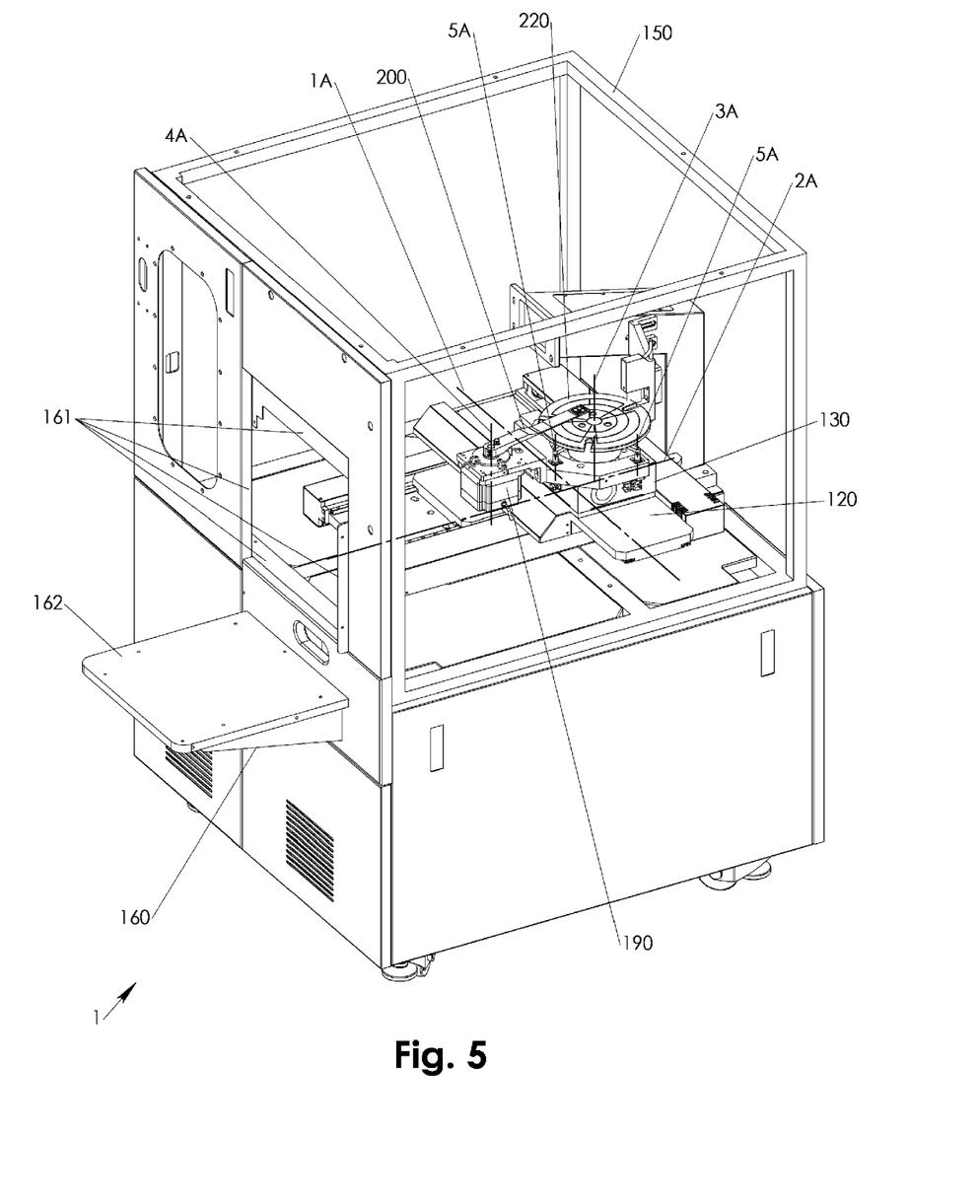
FIG. 5 is a second perspective view of the device of FIG. 4.
Figure 6:
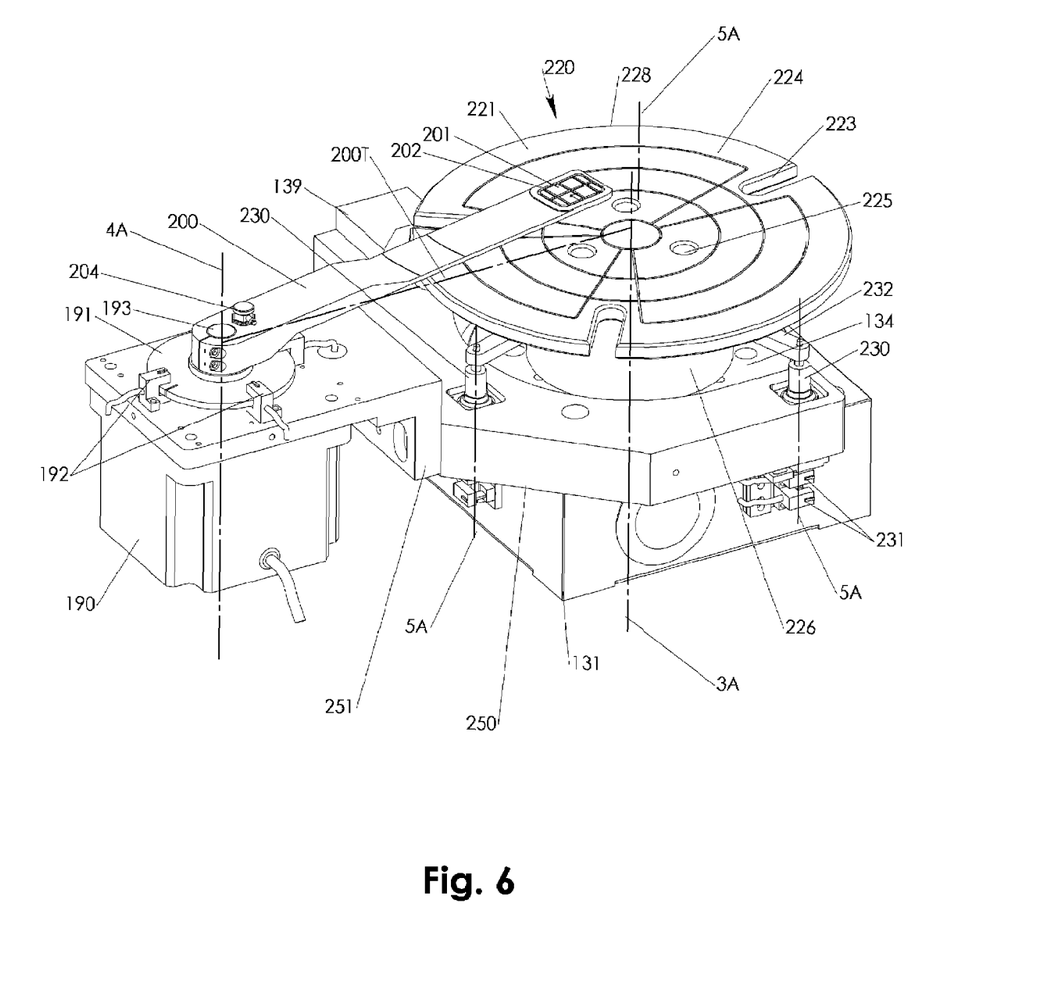
FIG. 6 is the second perspective view of a stage mounted subassembly of the above FIGS. 1-5.

On the base plate 151 is mounted a head support 141, which holds an optical testing head 140. Also mounted to the base plate 151 is a well known precision X-Y stage 120 having a preferred travel of about thirteen inches along a first linear chuck positioning X-axis 1A and along a second linear chuck positioning axis Y-axis 2A as depicted in FIGS. 4-6. A rotary stage 130 is combined with and on top of the X-Y stage 120 providing a third rotational chuck positioning axis 3A also shown in FIGS. 4-6. The rotary stage 130 has a base 131 that may house a worm gear driven by an attached well known stepper motor 139 shown in FIG. 7. The base 131 may have a height 131H of about 2¼ inches and may have a square base contour of about six by six inches base width 131W. A rotating flange plate 134 on top of the base 131 may have a diameter of about 5½ inches and may feature attachment/positioning holes 135 and a central alignment recess 136 also shown in FIG. 7.

Also attached to the X-Y stage 120 preferably via rotary stage C-fixture including a flange angle 251 attached to a base top C-flange 250 is a motion controlled effector rotation device in the preferred configuration of a geared stepper motor 190. The motion controlled effector rotation device provides a fourth vertical effector rotation axis 4A and rotates an effector 200 flanged preferably on a stepper motor shaft 193 shown also in FIG. 6. The rotary stage C-fixture attaches rigidly to the top of the rotary stage base 131 while providing access to the flange plate 134.

The effector 200 has an object holding face 201 that centrally holds the flat object 2 bottom during the cassette-chuck transfer in a well known vacuum assisted fashion. For that purpose, the object holding face 201 features vacuum distribution grooves 202 that connect to a vacuum access flange 204 in close proximity to the fourth axis 4A. Via the vacuum access flange 204, a vacuum may be peripherally provided to the object holding face 201 as is well known to anyone skilled in the art. The effector rotation device 190 may be a hollow shaft rotary actuator like a DG Series Rotary Actuator made by Oriental Motor™. In that case, vacuum may be accessed to the effector 200 through the hollow shaft.

Concentrically attached to the stepper motor shaft 193 may be an angular position indicator disc 191 monitored by effector position sensors 192 for a computer motion controlled rotation of the effector 200 between a chuck-effector transfer orientation 200T shown in FIG. 7 and at least one effector-cassette transfer orientation of the effector 200. An effector length 200R is selected and the fourth axis 4A is positioned on the X-Y stage with respect to the third axis 3A and in conjunction with the effector length 200R such that the effector 200 may have a reach 200E beyond the overall footprint 150W by 150D. The effector 200 may thereby centrally access with its object handling face 201 a flat object 2 having the maximum contour-center distance CMAX within a cassette 170 while the cassette 170 may be vertically moved within the cassette elevator 180. The effector 200 may also rotationally position the flat object 2 with respect to the X-Y stage into substantial concentric alignment with the third axis 3A. The effector length 200R may be about 8 inches, which is also the approximate distance between third axis 3A and fourth axis 4A. The effector reach 200E may be about 6½ inches. In the depicted embodiment of the invention, a flat object 2 having a maximum contour-center distance CMAX of about 4 inches such as a 200 mm diameter wafer may be conveniently transferred from/to the peripheral cassette 170 via a cassette elevator 180 configured as SMIP loadport. The fourth axis 4A may be repositioned with respect to the third axis 3A in conjunction with an extended effector length 200R for the purpose of handling flat objects 2 of 300 mm diameter as is clear to anyone skilled in the art.

The effector 200 has preferably a straight blade like configuration for sufficient spacing between flat objects 2 stacked on top of each other in the cassette 170 while providing balanced stiffness against torsional deformation. A total effector movement range 201B in combination with full travel of the X-Y stage along first and second axes 1A, 2A and full effector 200 rotation around fourth axis 4A is indicated in FIG. 4. As can be seen in FIG. 4, the total effector movement range 201B extends laterally beyond the interface base 162. Optionally a second cassette elevator docking interface may be positioned along the frame front 155 adjacent the interface base 162. Clearly, the fourth axis 4A may be positioned with respect to the third axis 3A other than parallel to second axis 2A. For example, the fourth axis 4A may be positioned in a 45 deg angle with respect to the first axis 1A, which would result in the total effector movement range 201B to also extend beyond one of the frame sides 156, 157. The effector length 200R and axis 3A/4A spacing may be adjusted for a predetermined effector reach 200E.

A fifth vertical chuck-effector transfer axis 5A is provided by at least three motion controlled pin lifters 230, which are preferably combined with the X-Y stage 120 via the base top C-frame 250 and the rotary stage base 131. As shown in FIG. 7, each of the pin lifters 230 has an object lifting face 234, which together define an object carrying boundary 234B that encompasses a gravity center safety offset area 220C while the flat object 2 is in a chuck-effector transfer orientation 200T indicated in FIG. 7 by a dot-dashed line representing a centerline of the effector 200. At the chuck-effector transfer orientation 200T the object holding face 201 is substantially centered with respect to the third axis 3A. The pin lifters 230 are preferably individually electrically actuated.

The gravity center safety offset area 220C accounts for varying clamping positions of a flat object 2 vacuum clamped on the object holding face during transfer from the cassette 170 into the chuck-effector transfer orientation 200T. Varying clamping positions may result from positioning errors of wafers within the cassette 170, stiction of the flat object 2 in the cassette 170 tray, acceleration forces during object transfer and the like. The gravity center safety offset area 220C may also account for discrepancies between a center of gravitation and a geometrical center of the flat object, which is preferably held in its geometrical center by the object holding face 210. The encompassing of the gravity center safety offset area 220C by the object carrying boundary 234B warrants safe transfer between the object holding face 201 and the object lifting faces 234. Additional transfer safety may be accomplished by vacuum assisted fixing of the object lifting faces 234 on the transferred flat object's bottom.

To provide unimpeded rotation of the preferably straight effector 200 into the chuck-effector transfer orientation 200T, the pin lifters 230 are fixed with respect to the X-Y stage 120 on the base 131 and have shafts that extend within the base height 131H where pin lifter position sensors 231 sense the pin lifters' 230 end positions. The pin lifters 230 are preferably circumferentially arrayed with respect to the rotary stage base 131 in a number of three. One of the three pin lifters 230 is closest to the fourth axis 4A with its respective object lifting face 234 in an offset 2340 to the chuck-effector transfer orientation 200T such that the effector 200 remains in minimum distance to the respective object lifting face 234 while in the chuck-effector transfer orientation 200T. The second and third pin lifters 234 are positioned with their respective object lifting faces 234 along a line 234B1 of the object carrying boundary 234B that is about perpendicular with respect to the chuck-effector transfer orientation 200T. In that way, the object carrying boundary 234B can be brought to a maximum with only three employed pin lifters 230.

First, second, third, fourth and fifth axes, 1A-5A together with their respective X-Y stage 120, rotary stage 130, motion controlled effector rotation device 190, pin lifters 230, cassette elevator docking interface and a cassette elevator controller define a five axis wafer handling system of the testing device 1. In case of a fully integrated and/or custom cassette elevator 180 built and combined in conjunction with the testing device 1, a sixth cassette elevator axis 6A may be part of a six axis wafer handling system. The integrated cassette elevator may be integrated by well known structural elements other than the cassette elevator docking interface 160. The five axes 1A-5A and cassette elevator 180 or the six axes 1A-6A may be computer controlled as is well known in the art.

As also shown in FIG. 6, a chuck 220 is mounted in a quick exchange connection on the flange plate 134. The quick exchange connection may include an approximate horizontal positioning feature including central screw attachment holes 225 corresponding to attachment/positioning holes 135 for an at least horizontal and circumferentially approximate quick attachment of the chuck 220 to the flange plate 134. The gravity center safety offset area 220C accounts via well known machine screws. Part of the quick exchange connection may also be a well known centering feature corresponding to the central alignment recess 136.

The chuck 220 is employed for fixedly holding one of the multiple contours flat objects. As part of a precision vertical positioning feature, the chuck 220 may have a chucking face 221 in precise planarity to a bottom contact face configured for snugly contacting the flange plate 134. Once the chuck 220 is tightened on the flange plate 134, the chucking face 221 is highly plan parallel with respect to the flange plate 134. The chucking face 221 may have also well known vacuum distribution grooves 221 for vacuum assisted object clamping. As shown in FIG. 3, the chucking face 221 is vertically positioned with respect to a through beam edge detector sensor 210 and the chuck 220 has a peripheral chuck height 220H such that the chuck 220 fits within a measurement height 210H of the through beam sensor 210 during a chuck calibration routine in which the rotational orientation of the chuck 220 with respect to the flange plate 134 may be determined.

An outside boundary 228 of the chuck 220 may be in an inward offset to one of the multiple contours of a flat object 2 predetermined for inspection on the chuck 220. In that way and as shown in FIGS. 1-5, a through beam edge detector sensor 210 may perform the well known object position calibration via optical detection of the fixed object's edge extending beyond the chuck's 220 outside boundary 228. The edge detector sensor 210 is preferably combined with the testing device 1 via a mounting bracket 211 attached to the head support 141. The through beam sensor 210 is horizontally positioned in conjunction with the maximum contour-center distance CMAX of preferably about six inches and the minimum contour-center distance CMIN of preferably about three inches while one of the multiple contours flat objects 2 is fixed on the chuck 220. As a result, the on-chuck position calibration may be performed by the through beam edge detector 210 in conjunction with a combined movement of the chucked flat object 2 along the first axis 1A, second axis 2A via the X-Y stage 120 and around the third axis 3A via the rotary stage 130. A preferably employed sensor 210 may be a LED type wafer alignment sensor HD-T1 series made by SUNX™.

Multiple versions of the chuck 220 with varying shape and/or diameter of the outside boundary 228 may be alternately fixed to the flange plate 134 to accommodate the multiple contours flat objects. The object lifting faces 234 to the contrary are constant in their position and sufficiently close to the third axis 3A to lift a flat object 2 having a minimum contour-center distance CMIN of about three inches. For that purpose, each of the multiple version chucks 220 has vertical through holes 223 extending through the chucking face. The vertical through holes 223 correspond at least to respective object lifting faces 234 in an object receiving orientation of the chuck 220. The object receiving orientation is a chuck 220 orientation around the third axis 3A such that during chuck-effector transfer of a flat object 2 the chuck 220 is rotationally oriented such that at least the object lifting faces 234 may be vertically moved through the corresponding through holes 223. The vertical through holes 223 may be open towards the outside boundary 228 of the chuck 220 as depicted in the figures.

In the preferred case depicted in the Figures, the base contour 131W by 131W has a minimum rotary center distance of about three inches, which is half the base width 131W. Since the pin lifters 230 extend within the base height 131H, they are assembled in a minimum pin center distance 230D with respect to a vertically projection of the base contour 131W by 131W as shown in FIG. 7. The combined minimum rotary center distance and minimum pin center distance 230D are substantially larger than the minimum contour-center distance CMIN of about three inches of a 150 mm wafer or 6"×6" photomask. Nevertheless and in order to provide positive lifting contact of the object lifting faces 234 with the object bottom face even in case of a minimum contour-center distance CMIN of about three inches, the pin lifters 230 may feature pin offset arms 232. The pin offset arms 232 are radial inward offsetting the respective object lifting face 234 towards the third axis 3A such that the object lifting faces 234 may lift objects within the minimum contour center distance CMIN.

The pin offset arms 232 may extend into the chuck 220 in a raised pin position at which the object lifting faces 234 are above the object holding face 201. In that case, the vertical through holes 223 may correspond also to the pin offset arms 232 such that the pin offset arms 232 may unimpeded move through the body of the chuck 220. The chuck 220 may have a reduced diameter below the peripheral height 220H such that it may be rotated unimpeded by the lowered pin lifters 230.

Once one of the multiple contours flat objects 2 is selected for optical inspection within the testing device 1, a corresponding one of the multiple chucks 220 is selected and attached to the flange plate 134. During an eventual chuck calibration routine the rotational orientation of the chuck 220 with respect to the flange plate 134 is verified such that an unimpeded movement of the pin lifters 230 through the vertical through holes 223 is warranted. flat objects 2 may be provided via a cassette 170 to the cassette elevator 180 in a well known fashion. To transfer a flat object 2 from the cassette 170 onto the chuck 220, the cassette elevator 180 lowers the cassette 170 into predetermined vertical position while the effector 200 is rotated into the cassette-effector transfer orientation. In a following step, the X-Y stage 120 moves the effector beneath the predetermined flat object 2 previously brought into corresponding vertical position with sufficient clearance by the cassette elevator 180. Once the object holding face 201 is positioned by the X-Y stage 120 centrally beneath the flat object 2 to be transferred, the cassette elevator 180 lowers the cassette 170 until the flat object 2 fully rests on the object holding face 201 and is released from its cassette 170 slot. A vacuum is applied to clamp the flat object 2 and the effector 200 is moved out of the cassette 170 with sufficient clearance for a free rotation of the effector 200 together with the clamped flat object 2 into chuck-effector transfer orientation 200T. The chuck 200 is meanwhile brought into pin lifter raising orientation and the pin lifters 230 freely move through the through holes 223 to lift the flat object 2 from the effector 200 after the vacuum has been turned off in the object holding face 201. The effector 200 is rotated into a parking position and the flat object 2 is then lowered onto the chucking face 221 and vacuum assisted clamped. The outer edge of the flat object 2 extends sufficiently beyond the outside boundary 228 of the chuck 220 for a well known position calibration of the flat object 2 by the edge detector through beam sensor 210. During the object position calibration, the X-Y stage 120 moves the flat object 2 with its edge within range of the sensor 210. In a following step, the sensor 210 takes measurements while the rotary stage 130 rotates the flat object 2 to determine precise position and angular orientation of the flat object 2 with respect to the X-Y stage 120 and the rotary stage 130. After position calibration, the flat object 2 is moved beneath the optical testing head 140 to perform the predetermined well known optical measurements and inspections. After completion, the flat object 2 is released from the chucking face 221 and transferred back to its slot in the cassette 170 in reverse order of the steps described above for transferring the flat object 2 from the cassette 170 onto the chuck 220.

Accordingly, the scope of the invention described in the figures and the specification above is set forth by the following claims and their legal equivalent:

What is claimed is:

1. A compact multiple contours flat objects surface testing device comprising an on-chuck object calibration system and an integrated cassette-chuck transfer system, wherein each of said multiple contours flat objects has one of a maximum contour-center distance and a minimum contour-center distance, said on-chuck object calibration system and said integrated cassette-chuck transfer system being provided by:
   a. A five axes wafer handling system, said five axes consisting of:
      i. A first linear chuck positioning axis and a second linear chuck positioning axis provided by an X-Y stage mounted on said device, said X-Y stage having an X-travel along said first axis and a Y-travel along said second axis;
      ii. A third rotational chuck positioning axis provided by a rotary stage combined with and on top of said X-Y stage;
      iii. A fourth vertical effector rotation axis provided by a motion controlled effector rotation device combined with said X-Y stage, wherein said effector rotation device motion controlled rotates an object handling face of an effector attached to said motion controlled effector rotation device;
      iv. A fifth vertical chuck-effector transfer axis provided by at least three motion controlled pin lifters combined with and fixed at said X-Y stage, each of said at least three motion controlled pin lifters being constant in its position with respect to said X-Y stage and circumferentially arrayed with respect to said rotary stage, each of said pin lifters having an object lifting face that is sufficiently close to said third rotational chuck positioning axis to lift said flat object having said minimum contour-center distance, said object lifting faces together defining an object carrying boundary encompassing a gravity center safety offset area while said effector being in a chuck-effector transfer orientation with said object handling face being substantially centered with respect to said third rotational chuck positioning axis;
      v. a cassette elevator docking interface;
      vi. a cassette elevator controller;
   wherein a length of said effector is selected and said fourth axis is positioned on said X-Y stage with respect to said third axis and in conjunction with said effector length such that said effector may comprise an effector reach that is reaching beyond an overall footprint of said compact multiple contours flat objects surface testing device, said effector reach having at least a length such that said effector may centrally access a flat object having said maximum contour-center distance within said cassette vertically moved within said cassette elevator peripherally attached to said docking interface, and such that said effector may rotationally position said flat object with respect to said X-Y stage into substantial concentric aligned with said third axis;

b. a chuck having a chucking face for fixedly holding one of said multiple contours flat objects, said chuck comprising vertical through holes that are extending through said chucking face and that correspond at least to respective ones of said object lifting faces in an object receiving orientation of said chuck; and c. a through beam edge detector sensor combined with said device and horizontally positioned in conjunction with said maximum contour-center distance and said minimum contour-center distance while one of said multiple contours flat objects is fixed on said chuck such said one of said multiple contours flat objects may be said on-chuck position calibrated by use of said through beam edge detector sensor in conjunction with a combined movement of said one of said multiple contours flat objects along said first axis, said second axis and around said third axis.

2. The multiple contours flat objects surface testing device of claim 1, wherein said multiple contours flat objects include:

a. a 150 mm wafer having said minimum contour-center distance of about 3 inches; and b. a 200 mm wafer; having said maximum contour center distance of about 4 inches.

3. The multiple contours flat objects surface testing device of claim 2, wherein said X-travel is up to about 13 inches and said Y-travel is up to about 13 inches.

4. The multiple contours flat objects surface testing device of claim 3, wherein an overall footprint of said multiple contours flat objects surface testing device is up to about 33 by 34 inches.

5. The multiple contours flat objects surface testing device of claim 1, wherein said effector rotation device is a stepper motor and said object effector is mounted on a shaft of said stepper motor.

6. The multiple contours flat objects surface testing device of claim 1, wherein said effector rotation device has a hollow shaft and wherein vacuum is accessed to said effector through said hollow shaft.

7. The multiple contours flat objects surface testing device of claim 1, wherein the center of said object holding face has a load arm distance to said fourth axis of about 8 inches, wherein said effector reach is about 6½ inches, and wherein said load arm distance substantially equals a distance between said third axis and said fourth axis.

8. The multiple contours flat objects surface testing device of claim 1, wherein said effector is substantially straight, wherein said at least three motion controlled pin lifters are in a number of three, wherein one of said three pin lifters closest to said fourth axis is in an offset to said chuck-effector transfer orientation such that said effector remains in minimum distance to an object lifting face of said closest pin lifter while said effector is in said chuck-effector transfer orientation, and wherein a second and a third of said three pin lifters have their respective ones of said object lifting faces positioned along a line of said object carrying boundary that is about perpendicular with respect to said chuck-effector transfer orientation.

9. The multiple contours flat objects surface testing device of claim 1, wherein said rotary stage comprises a base contour having a minimum rotary center distance to said third axis, wherein at least one of said at least three motion controlled pin lifters has a minimum pin center distance to a vertically projection of said base contour, wherein said combined minimum rotary center distance and said minimum pin center distance are substantially larger than said minimum contour-center distance, and wherein said at least one of said at least three motion controlled pin lifers includes a pin offset arm radial inward offsetting with respect to said third axis said object lifting face within said minimum contour-center distance.

10. The multiple contours flat objects surface testing device of claim 9, wherein said pin offset arm extends into said chuck in a raised pin position and wherein said vertical through hole corresponds to said pin offset arm.

11. The multiple contours flat objects surface testing device of claim 1, wherein said chuck being in a quick exchange connection with said rotary stage and wherein said quick exchange connection provides an approximate horizontal positioning feature and a precision vertical positioning feature, and wherein said chucking face is vertically positioned with respect to said through beam edge detector and said chuck has a peripheral height such that said chuck fits within a measurement height of said through beam edge detector sensor during a chuck calibration routine.

12. The multiple contours flat objects surface testing device of claim 1, wherein said cassette elevator is part of said multiple contours flat objects surface testing device.

* * * * *